(12) United States Patent
Syage

(10) Patent No.: US 7,299,710 B2
(45) Date of Patent: Nov. 27, 2007

(54) HAND-HELD TRACE VAPOR/PARTICLE SAMPLING SYSTEM

(75) Inventor: Jack A. Syage, Huntington Beach, CA (US)

(73) Assignee: Syagen Technology, Tustin, CA (US)

( * ) Notice: Subject to any disclaimer, the term of this patent is extended or adjusted under 35 U.S.C. 154(b) by 0 days.

(21) Appl. No.: 11/202,455

(22) Filed: Aug. 11, 2005

(65) Prior Publication Data

US 2007/0034024 A1 Feb. 15, 2007

(51) Int. Cl.
*G01N 1/22* (2006.01)
(52) U.S. Cl. .................... 73/863.12; 73/863.23; 73/864.34; 73/28.04; 73/29.05; 73/31.02; 73/31.03; 73/31.07
(58) Field of Classification Search ........... 73/28.04, 73/29.05, 31.02, 31.03, 31.07, 863.12, 863.23
See application file for complete search history.

(56) References Cited

U.S. PATENT DOCUMENTS

| | | | | | |
|---|---|---|---|---|---|
| 4,580,440 A | * | 4/1986 | Reid et al. | .................. | 73/31.07 |
| 4,718,268 A | * | 1/1988 | Reid et al. | .................. | 73/19.01 |
| 4,987,767 A | * | 1/1991 | Corrigan et al. | ........... | 73/23.36 |
| 5,214,952 A | * | 6/1993 | Leggett et al. | ............... | 73/1.03 |
| 5,345,809 A | * | 9/1994 | Corrigan et al. | ............. | 73/23.2 |
| 5,400,665 A | * | 3/1995 | Zhu et al. | ................ | 73/863.12 |
| 5,465,607 A | * | 11/1995 | Corrigan et al. | ........... | 73/23.36 |
| 5,855,652 A | * | 1/1999 | Talley | ........................... | 96/44 |
| 5,914,454 A | * | 6/1999 | Imbaro et al. | ................. | 95/64 |
| 5,915,268 A | * | 6/1999 | Linker et al. | ................ | 73/23.2 |
| 2005/0160838 A1 | * | 7/2005 | Weaver | ................... | 73/863.03 |
| 2005/0241416 A1 | * | 11/2005 | DeFriez et al. | .......... | 73/863.12 |

\* cited by examiner

*Primary Examiner*—Hezron Williams
*Assistant Examiner*—Samir M. Shah
(74) *Attorney, Agent, or Firm*—Ben J. Yorks; Irell & Manella LLP

(57) ABSTRACT

A sampling system that contains filter components for collecting and concentrating vapor and particles in high-volume flows. The sample is then vaporized and delivered to a detector at a low-volume flow. The invention also has a sampling probe that contains an air-jet to help dislodge particles from surfaces and a heating lamp to help vaporize compounds on surfaces or objects. The sampling system is especially useful for screening for explosives and other illicit chemicals and toxins on people, baggage, cargo, and other objects.

9 Claims, 7 Drawing Sheets

HAND-HELD TRACE VAPOR/PARTICLE SAMPLING SYSTEM

BACKGROUND OF THE INVENTION

1. Field of the Invention

The present invention relates to the field of detection apparatus used to screen for the presence of explosives and other chemical entities.

2. Background Information

An effective screening system for threat compounds such as explosives as well as chemical and biological weapons must be able to collect, concentrate, and analyze trace samples quickly and accurately. Many detection technologies (e.g., mass spectrometry, ion mobility spectrometry, optical spectroscopy, etc.) have been developed over the years and trace detectors now exist that can detect a wide range of explosives and chemical weapons, and to a lesser extent biological weapons. Much less attention has been given to collecting and delivering sample to the detectors, yet this is arguably the most challenging part of a screening system since it must adapt to a wide range of applications and screening scenarios. Furthermore, whereas the specificity of a detector is the key to minimizing false positive rates, the collector/concentrator is of vital importance for maximizing detection rates, since if a trace sample is not delivered to the detector, it will result in a non-detect event.

An effective sampling system must have the following operational characteristics: (1) access the volume containing the contamination, (2) dislodge the contamination, particularly for particles that can stick tightly to materials, (3) concentrate collected vapor and particle material, (4) deliver the material to a trace detector in a step that involves vaporization, and (5) minimize cycle time and carryover effects.

An effective collector/concentrator sampling system for explosives and other threats must be able to collect vapor and particles, and if delivering to a trace detector, convert the particles to vapor. Several vapor and particle sampling systems have been developed in the past, however, they are either optimized for one or the other phase, or are not suitable for trace detectors.

U.S. Pat. No. 6,087,183 issued to Zaromb discloses a method to collect vapor and particles on a liquid film. However, a liquid concentrate is not the preferred medium for a trace detector, which is designed to analyze vaporized sample. U.S. Pat. No. 5,914,454 issued to Imbaro et al. discloses a spray of charged droplets to collect vapor, liquid, and particles, but the sample is also concentrated in a liquid. U.S. Pat. No. 5,855,652 issued to Talley discloses a method for collecting particles and microorganisms into a water sample. U.S. Pat. No. 4,092,218 issued to Fine et al. discloses a method for the selective detection of explosives vapors, but does not show that it is capable of collecting particles.

A series of patents issued to Linker et al. disclose methods to collect explosives particles for trace detectors that have some capability to collect vapor as well. U.S. Pat. No. 6,345,545, issued to Linker et al., discloses a two-stage preconcentrator that uses a metal or other electrically conducting screen to capture particles. Some vapors may also stick to the screen, however, the surface chosen for particle collection is not in general optimal for vapor collection. U.S. Pat. No. 6,523,393, issued to Linker et al., discloses a hand-portable embodiment of the metal screen particle concentrator that makes use of a removable screen that is manually placed first in the high volume flow region and second in the detector region.

The above patents disclose means for sample concentration. Another important component to an overall screening system is a sampling probe for collecting vapor and particles, particularly from hard-to-remove locations and surfaces. U.S. Pat. Nos. 6,334,365 and 5,915,268 issued to Linker et al., disclose the use of air-jets to help dislodge particles from the clothing of individuals in a portal device for screening people for explosives. U.S. Pat. No. 6,708,572, issued to Jenkins et al., also discloses the use of air-jets to dislodge particles from individuals in a portal device.

Trace detectors are extensively used in airports and other venues to screen baggage for explosives. The method typically used to remove material from surfaces are swipes of cloth. This method is effective at collecting residue, however, it requires manual operation and therefore may produce unpredictable results in the collection process. Furthermore it is not effective at collecting vapors.

BRIEF SUMMARY OF THE INVENTION

A concentrator that collects and transfers a sample. The concentrator includes a vapor filter and a particle filter. The particle filter is heated to a temperature that also heats the vapor filter.

DETAILED DESCRIPTION

Disclosed is a sampling system that contains filter components for collecting and concentrating vapor and particles in high-volume flows. The sample is then vaporized and delivered to a detector at a low-volume flow. The invention also has a sampling probe that contains an air-jet to help dislodge particles from surfaces and a heating lamp to help vaporize compounds on surfaces or objects. The sampling system is especially useful for screening for explosives and other illicit chemicals and toxins on people, baggage, cargo, and other objects.

Figure 1:
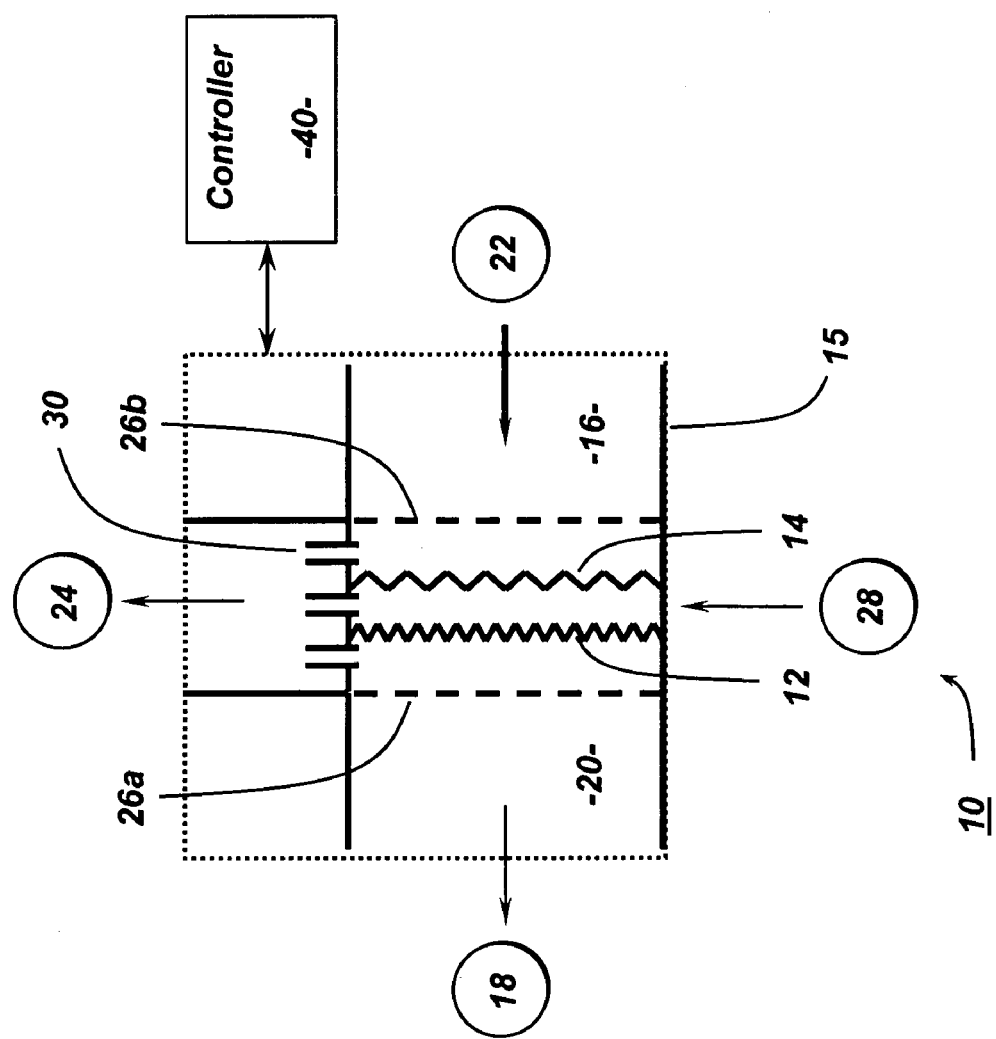
FIG. 1 is an illustration of vapor/particle concentrator.

Referring to the drawings more particularly by reference numbers, FIG. 1 shows an embodiment of a collection system 10. The system 10 includes porous filters 12 and 14 for the collection of vapors and particles, respectively. The filters 12 and 14 are coupled to a housing 15. Particle and vapor sample in region 16 is pulled through the filters 12 and 14 by a pump 18 in region 20. The particle and vapor in region 16 may be enhanced by a device 22 for removing and collecting the sample from remote locations. Filters 12 and 14 have reasonably large area and porosity in order to allow a high volume of flow to pass through the filters. The filter diameters could typically range from ¼ inch to several inches in size. It is preferable to have the particle filter first so that particles are not trapped on the vapor filter. Some vapor sample may partially stick to the particle filter, however, the vapor filter is optimized for vapor collection and would collect all or most of the vapor in the air flow.

After a period of time for collecting vapor and particles, the concentrator 10 is then switched to a mode to deliver a sample to a detector 24. Valves or shutters 26a and 26b may be used to close off and isolate the filters 12 and 14 from regions 16 and 20. The filters 12 and 14 are then heated to vaporize the collected vapor and particles. One version of a particle filter is a screen or mesh made of metal or other electrically-conducting material. This type of filter is desirable because it can be rapidly heated by passing a current through it. The heating vaporizes the particles. The current may be provided by the controller 40. The vapor filter can be constructed from a non-electrically conducting material such as a polymer or similar material known for having a high adsorption coefficient for vapors. In order to remove the vapor, the vapor filter must also be heated. This can be achieved by the heat from the particle filter. The particle filter essentially acts as a "toaster" to heat the vapor filter to remove the vapor.

The system 10 may further contain a low-volume flow source 28 to transfer the vaporized collected sample to the detector 24. The system 10 may include a conduit 30 to the detector 24 which is an open tube, a series of apertures, or other means of fluid communication. The detector 24 can detect trace compounds within the sample. By way of example, the detector 24 may be a mass spectrometer or other detection system. The various elements of the system may be controlled by a controller 40.

Figure 2:
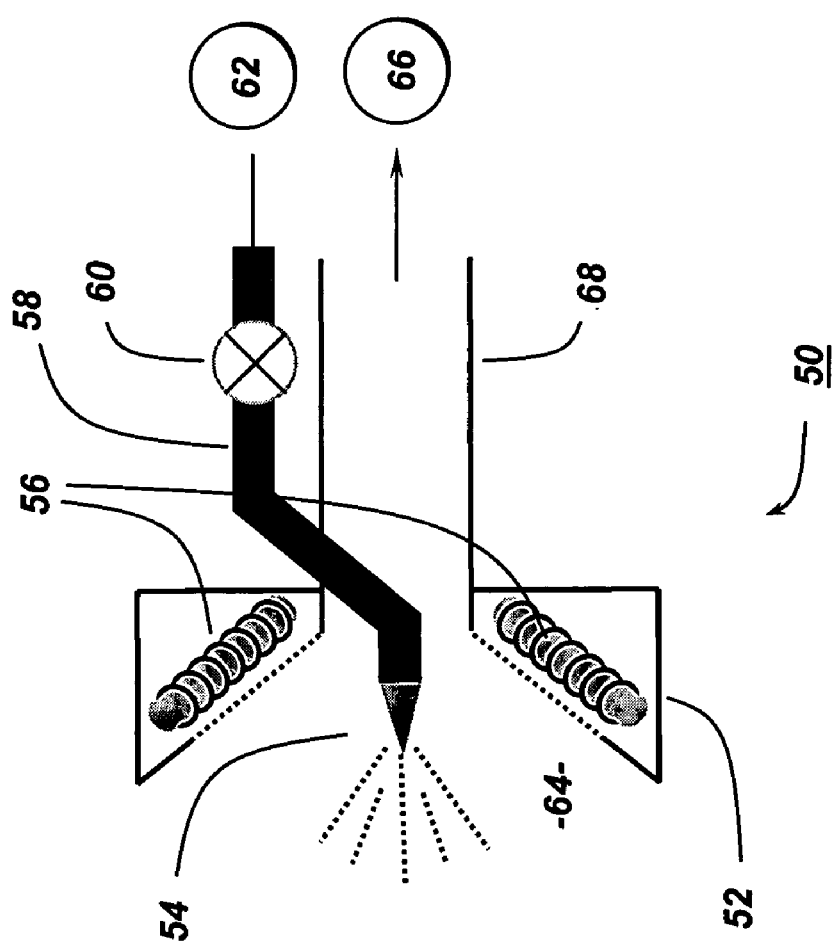
FIG. 2 is an illustration showing a sampling probe with an air-jet nozzle and heating lamps.

FIG. 2 shows an embodiment of a sampling probe 50 to enhance the collection of vapor and particles from surfaces or remote volumes. The probe includes a sampling head 52 that contains an air-jet nozzle 54. The head 52 may also include heating lamps 56. The air-jet nozzle 54 may be connected to a gas line 58, a shut-off valve 60 and a pump or compressor 62 that deliver a high-pressure flow of gas or air to the nozzle 54. The air-jet nozzle 54 may deliver gas pulses, or a continuous stream of gas. The air-jet nozzle 54 is used to help dislodge particles and residue from surfaces and objects such as baggage or people. Some chemicals on these objects may be liquids or have higher volatility than particles, such as some explosives and chemical weapons. In these cases it may be advantageous to apply heat to the surface or objects to raise the vapor pressure of these chemicals. This can be accomplished by turning on the heat lamps 56. By way of example the lamps 56 may be commercially available infrared lamps.

The air-jet nozzle 54 and lamps 56 are operated sufficiently long to remove sample from objects. The vapor and particle in region 64 is then drawn to a concentrator or other collection means by a pump 66 through a collection line 68. The concentrator may be the system shown in FIG. 1 of the drawings.

Figure 3:
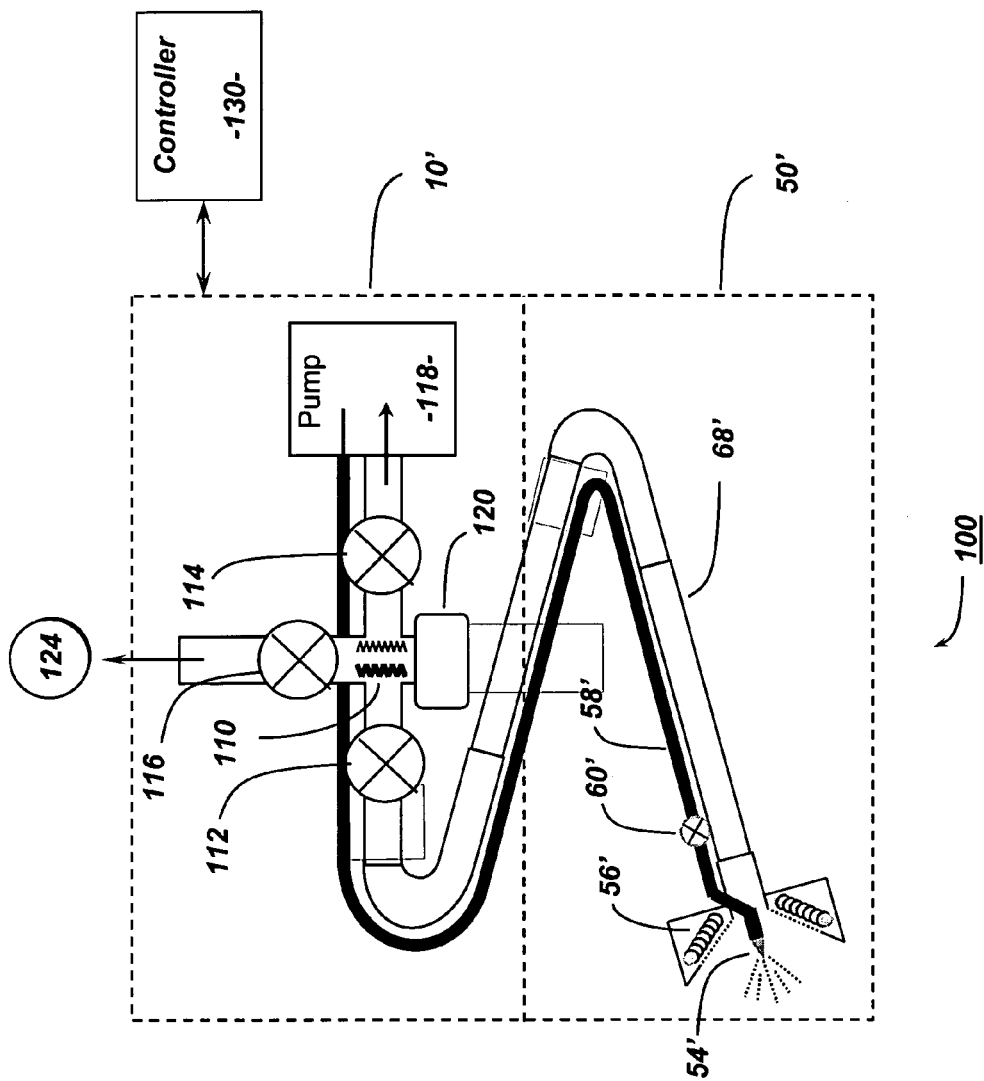
FIG. 3 is an illustration of a sampling system including a sampling probe and a vapor/particle concentrator coupled to a detector.

FIG. 3 shows an embodiment of sampling system 100 consisting of a sampling probe 50' and a concentrator system 10'. Similar to FIG. 2, the sampling probe 50' includes an air-jet nozzle 54', heating lamps 56', a pressured gas line 58' and a valve 60'. The sample is drawn to the concentrator 10' through sampling line 68'. The concentrator 10' in FIG. 3 consists of a vapor/particle filter assembly 110, valves 112, 114, and 116, pump 118, and a gas flow assembly 120. The pump 118 acts to supply an over-pressure of air or gas to the air-jet nozzle 54' and to pull the sample volume through the collection line 68'.

The sampling system 100 first collects sample by turning the pump 118 on, opening valves 112 and 114 and closing valve 116. During this period the air-jet nozzle 54' and lamps 56' operate as described relative to FIG. 2. After a sufficient sample collection time, the pump 118 may be deactivated, valves 112 and 114 may be closed, and valve 116 may be opened. The vapor/particle filter assembly is then heated in the manner described relative to FIG. 1 and a gas-flow from source 120 carries the vaporized sample to a detector or other device 124. It is also possible to operate 10' without the use of valve 116 if the volume of the line going to the detector 124 is relatively low and not open to the outside environment. All other operations would be the same. The operation and timing of the sampling system 100 is controlled by a controller 130.

Figure 4:
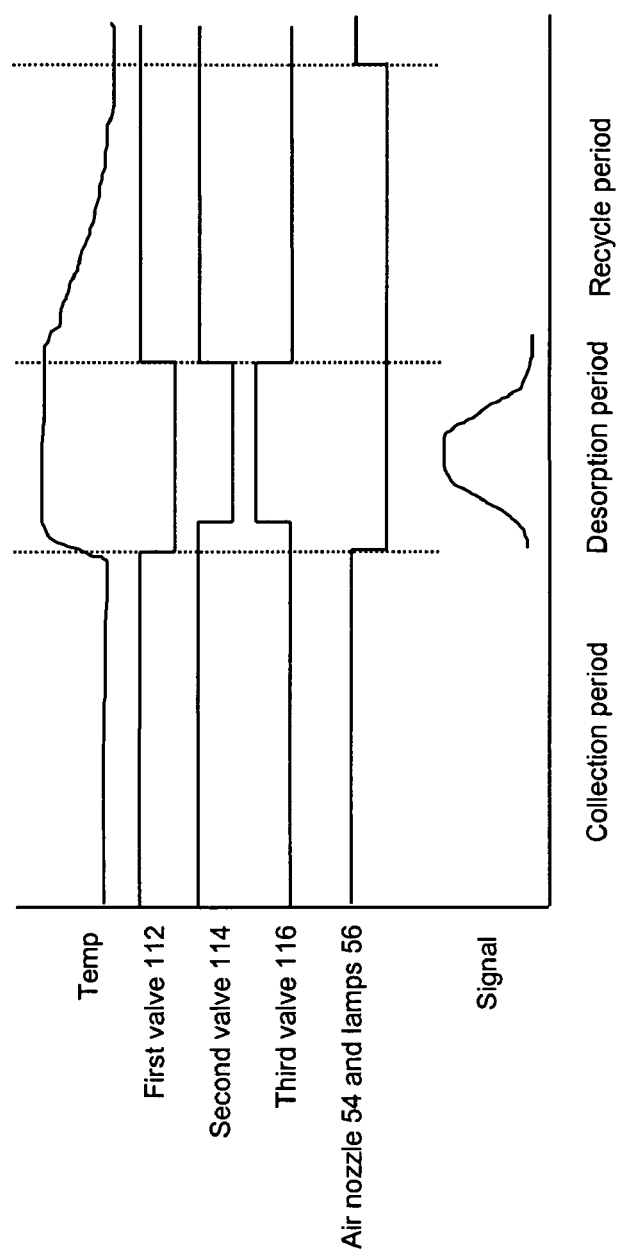
FIG. 4 is a timing diagram for the sampling system.

FIG. 4 shows a timing diagram for the sampling system 100. The high and low states in the diagram denote on and off for the respective components. As described above during the collection period the first and second valves 112 and 114 are open and the third valve 116 is closed. During this period the air nozzle 54 and lamps 56 may be operated. The collection period may range from about 1 second to a few minutes depending on the speed and sensitivity needed for a particular screening application. As noted above, following the collection period, valves 112 and 114 may be closed and valve 116 may be opened. The filter assembler is then heated and the concentrated sample thermally desorbs and flows to a detector, reaching a maximum concentration until all sample is desorbed. This step may typically take from about 1 second to about 1 minute.

It may be necessary to recycle the filter assembly following the desorption period after the sample has been delivered to the detector. This may be achieved by further heating the filter assembly to drive off remaining sample. For example if an explosives or other targeted chemical is collected in high concentration, it may be necessary to recycle the filter assembly a few times to remove remaining traces in order to be able to screen again at high sensitivity without having to worry about sample carryover from a previous screen. The recycle period may typically last from a few seconds to a few minutes. The recycle period also allows the filter assembly to cool down by initiating effectively a collection period sequence, but with the air nozzle 54 and lamps 56 in the off state. For fast screening it will be typical for the collection, desorption, and recycle periods to last only a few seconds each.

Figure 5:
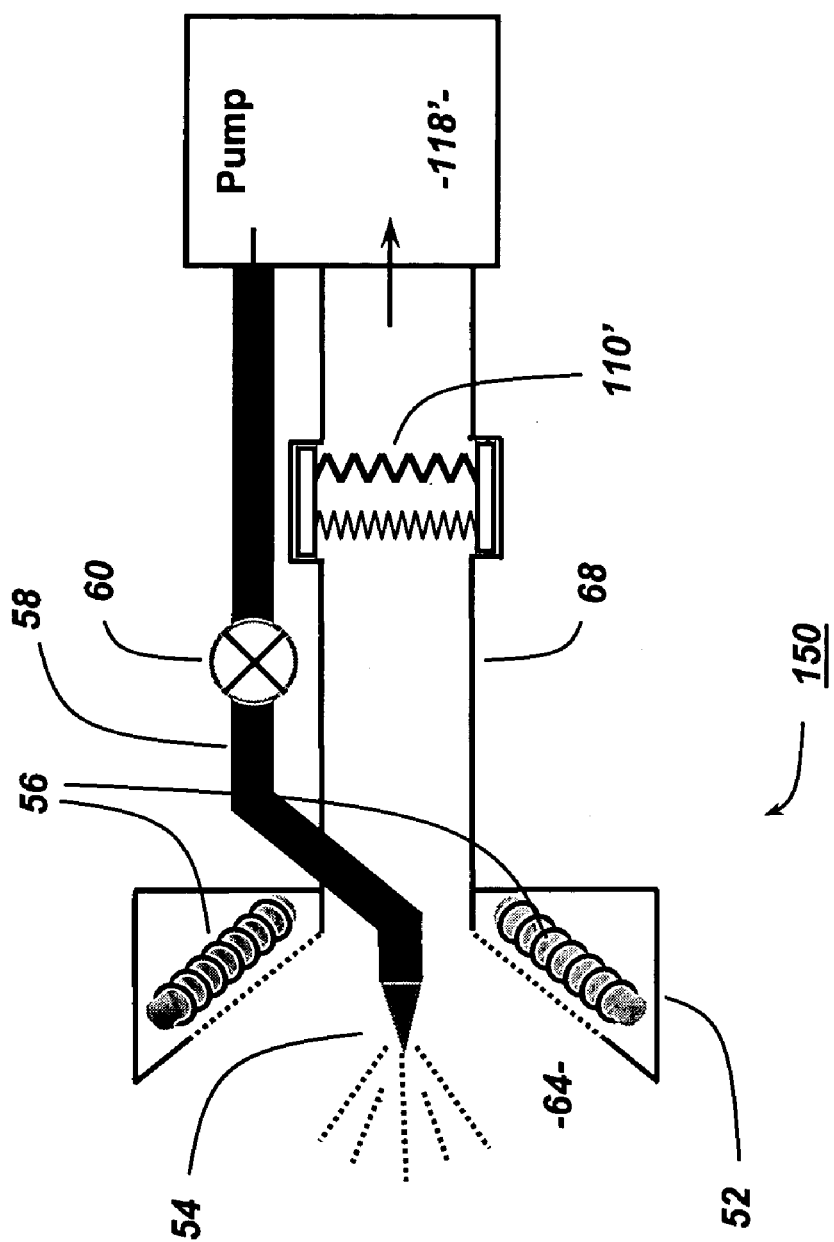
FIG. 5 is an illustration of an alternate embodiment of the sampling system.

It may be convenient to have separate assemblies for the sample collection phase and for the sample delivery phase. This would be the case where there is a need for several sampling devices with a single detector unit or when it is necessary to go to remote locations to collect sample. FIG. 5 shows an embodiment of a sampler and concentrator 150 that consists of a sampling probe 52, a vapor/particle filter assembly 110', a pump 118', and other components described relative to FIG. 2. This embodiment enables the sampler and concentrator assembly to be used away from the detector. It can also be made into a hand-held unit. One possible application is as a sampler for screening baggage for concealed explosives. The operation works similarly to that described for the sampling system 100 in FIG. 3, except that the device 150 in FIG. 5 does not deliver the concentrated sample to a detector or other device.

Figure 6:
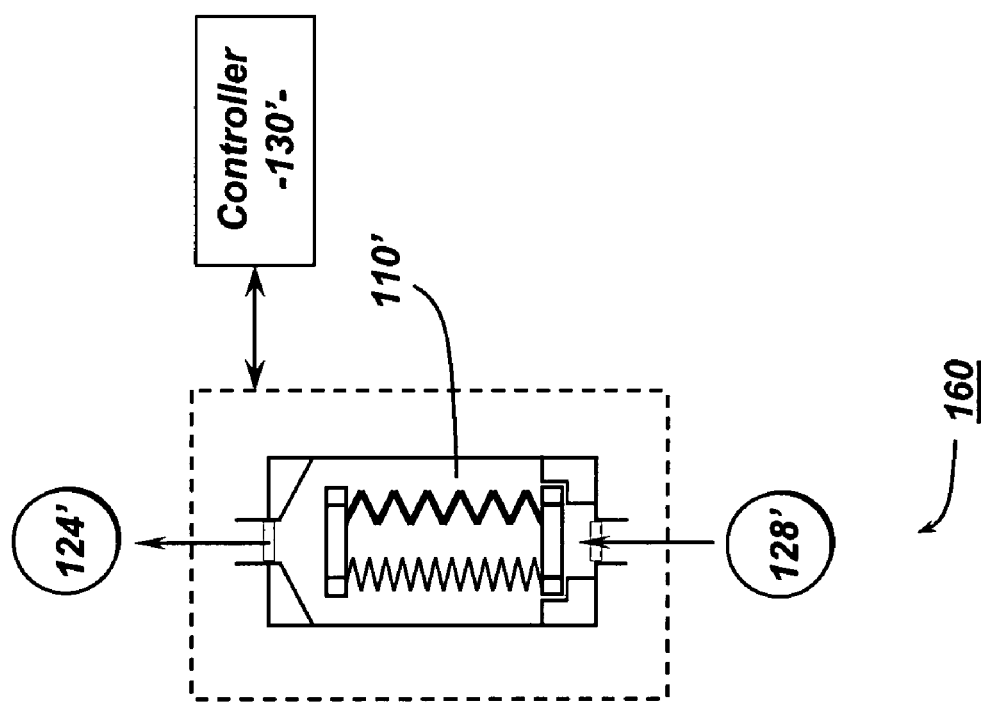
FIG. 6 is an illustration of a device for coupling a removable vapor/particle filter assembly to a detector.

FIG. 6 shows an embodiment of a device 160 that would enable delivery of concentrated sample from a vapor/particle filter assembly 110' to a detector 124'. The filter assembly 110' may be removed from the samples shown in FIG. 5. The filter assembly 110' is heated to desorb the collected vapor and particles in the manner described for concentrator 10. The device 160 may include a low volume source 128' that is controlled by controller 130'. Because the embodiment of 160 is not directly connected to the sample collection assembly, it is not necessary to have valves that isolate the filter assembly from the main flow.

Because the thermal desorption period and subsequent analysis by the detector typically takes much less time than the collection and recycling periods, the utilization of the combined sampler/concentrator/detector system can be improved by using multiple sampler/concentrator assemblies for a particular detector. A system may include several hand-held sampler/concentrator systems 150 that collect samples from multiple objects and then transfer the filter assembly 110' to the delivery and detector system 160. Because several filter assemblies may stack up waiting for analysis, it is necessary to have a system to keep track of the samples.

Figure 7:
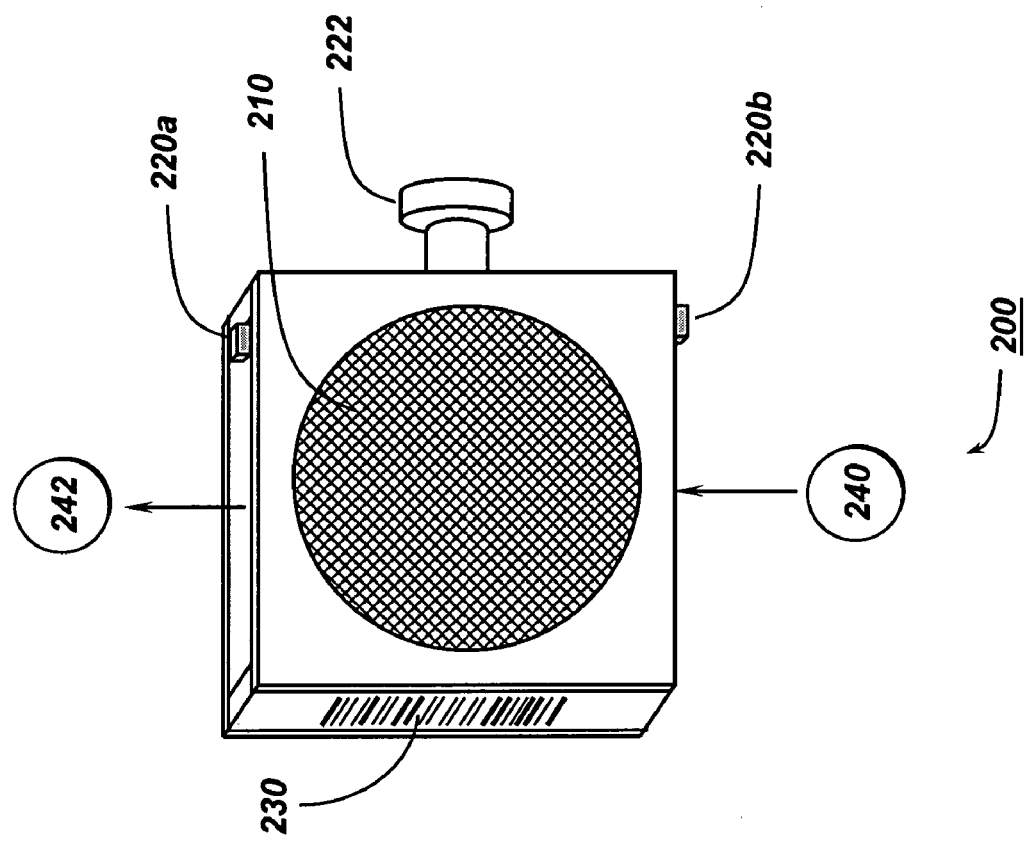
FIG. 7 is an illustration of a removable vapor/particle filter assembly.

FIG. 7 shows an embodiment of a removable and reusable vapor/particle filter assembly 200. The assembly 200 may include particle and vapor filter screens 210. The assembly 200 may also include electrical contacts 220a and 220b to provide connections to the particle electrically-conducting mesh for passing current to heat the mesh. To assist in transporting the filter screens 210 to the detector the assembly may include a handle 222. The assembly may include a bar code 230 that can be read to keep track of the samples.

When the filter assembly 200 is inserted into the delivery assembly 160, the pick-up flow of gas comes from source 240 and goes in the direction of 242 toward the detector. The bar code can also be used by either the sampler 150 or the delivery assembly 160 to keep count of the number of samples the filter assembly has been used for. This is convenient feature because it can alert operators to the end of the useful life of the filter assembly 200 or to a service and maintenance schedule.

For the hand-held sampler configuration 150, power may need to be provided by battery. By way of example we discuss typical pumping speeds, flow rates and concentration factors, as well as consumed power. Table I summarizes the air flow and power characteristics of the sample collector/concentrator.

TABLE I

| Concentrator specifications | Peak power consumption | |
|---|---|---|
| Collection flow × time: | IR lamps: | 50-100 W |
| 24 L/min × 5 s = 2.0 L | Pump: | 20-40 W |
| Detector flow × time: | Sampling line heater: | 15 W |
| 0.24 L/min × 5 s = 0.020 L | Valve: | 5 W |
| Concentration factor: | | |
| 5.0 L/0.0125 L = 100 | | |
| Cycle time: 20 s | | |
| (incl. 10 s recovery) | | |

The collection flow must draw the sampling volume over the surface or object, which we assume for this example to be about 2 L. The volume in the sampling line 68 (e.g., 3 cm ID×10 cm~0.1 L) is insignificant relative to the sampling volume and can be ignored. A small pump of 24 L/min can pull the 2 L sampling volume through the filter assembly 110' in 5-6 sec. Such a pump can be operated with about 10-20 W of power. For optimum use of the air-jet nozzle it may be preferable to use a larger pump. A 100 L/min blower pump consumes about 20-40 W of power. Many types of heating lamps 56 may be used. High efficiency IR lamps for device 150 would consume about 50-100 W when operated. If valve 60 is used and heating elements on the inside of the sampling line 68 are used, then there will be a need for another 20 W of power for a total peak power of 90-160 W. This peak power is operated for about 5 sec. per sample.

A nickel metal hydride battery, like a computer battery, delivers about 40 W hr per pound. A two pound battery would then give 30 min of 160 W peak power. At 5 sec. per sample this would give 360 samples. Assuming one sample is collected every minute, then the battery would last 6 hr. The values given above are by way of example only. Other choices of batteries and power management may be used to extend or change this period if necessary.

We now consider the concentration factor and potential sensitivity of the disclosed sampler embodiments particularly the sampler/concentrator 150 and the thermal desorber 160. The vapor and particle that is collected on the filter assembly 110' is thermally desorbed as a vapor. A flow rate of 0.12 L/min into the detector corresponds to an enrichment factor of 100× (Table I). If the internal volume of the filter assembly 110' and the volume of the inlet to the detector 124' is about 10 cm$^3$, then the flow needs to be on for 5 sec. to completely deliver the vaporized sample. In terms of total mass of compound collected, 1 part-per-billion of a target compound of MW 200 in the 2 L sampling volume in region 64 corresponds to about 16 ng. If a detector has a sensitivity of 16 pg, then a sensitivity at the sampling volume 64 of 1 part-per-trillion is possible. This sensitivity may be improved by extending the collection period to times longer than 5 s.

The systems and devices shown and described can be utilized to detect samples of trace explosives contamination on baggage, cargo, and personnel due to concealed explosive devices. Trace contamination is known to be pervasive throughout the bomb making and bomb packing process. This contamination can take the form of vapor for more volatile explosives (e.g., the class of nitrate esters and nitro toluenes, as well as taggant compounds) or particles for the more crystalline forms (e.g., the nitramines RDX and HMX).

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A concentrator that collects and transfers a sample that has a trace molecule to a detector, comprising:
 a housing with at least one passage to receive the sample;
 a vapor filter coupled to said housing, said vapor filter absorbs vapor from the sample;
 a particle filter coupled to said housing, said particle filter collects particles from the same sample;
 a controller that heats said particle filter to a temperature that also heats said vapor filter; and,
 a single detector that detects a vapor/particle sample created from the vapor absorbed by said vapor filter and the particles collected by said particle filter.

2. The concentrator of claim 1, further comprising a pump to pull the sample through said vapor and particle filters.

3. The concentrator of claim 2, further comprising a low-volume flow source to transfer the vapor/particle sample to a detector.

4. The concentrator of claim 1, further comprising a plurality of valves to control fluid flow about said vapor and particle filters.

5. The concentrator of claim 1, wherein said particle filter is constructed from an electrically conductive material.

6. The concentrator of claim 1, wherein said vapor filter is constructed from a non-electrically conductive material.

7. A method for collecting and transferring a sample with a trace molecule to a detector, comprising:

collecting at least one particle with a particle filter from the sample;

collecting a vapor with a vapor filter from the same sample;

heating the particle filter, the heating of the particle filter heats the vapor filter to create a vapor/particle sample; and, transferring the vapor/particle sample to a detector.

8. The method of claim 7, wherein the particle filter is heated with a current that flows through the particle filter.

9. The method of claim 7, wherein the particle and the vapor are collected when a first valve is open and a second valve is closed, and the vapor/particle sample is transferred when the first valve is closed and the second valve is open.

* * * * *